United States Patent [19]

Witek et al.

[11] 4,328,226
[45] May 4, 1982

[54] QUATERNARY BENZYLMORPHOLINE SALTS HAVING FORMYL OR NITRILE SUBSTITUENTS IN A RING AND FUNGICIDAL COMPOSITIONS

[75] Inventors: Stanislaw Witek; Damian Grobelny, both of Wroclaw; Jadwiga Gorska-Poczopko, Jablonna/k Warszawy; Edmund Bakuniak, Warszawa; Irena Bakuniak, Warszawa; Janina Ptaszkowska, Warszawa, all of Poland

[73] Assignee: Instytut Przemyslu Organicznego & Politechnika Wroclawska, Poland

[21] Appl. No.: 136,764

[22] Filed: Apr. 3, 1980

Related U.S. Application Data

[60] Continuation-in-part of Ser. No. 42,406, May 25, 1979, abandoned, which is a division of Ser. No. 954,305, Oct. 24, 1978, abandoned.

[30] Foreign Application Priority Data

Nov. 16, 1977 [PL] Poland .................................. 202199

[51] Int. Cl.³ .................... A01N 43/84; C07D 295/10
[52] U.S. Cl. ............................ 424/248.4; 424/248.58; 544/163; 544/167; 544/173; 544/174; 544/175
[58] Field of Search ............... 544/163, 167, 173, 174, 544/175; 424/248.4, 248.58

[56] References Cited

U.S. PATENT DOCUMENTS 2,566,535 9/1951 Ruddy ................................ 544/163

*Primary Examiner*—John M. Ford
*Assistant Examiner*—R. W. Ramsuer

[57] ABSTRACT

The present invention relates to the compounds having the following general formula (1)

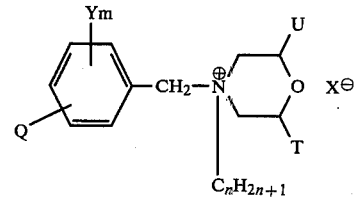

where:
  X is a halogen atom
  Q is a formyl or nitrile (cyano) group
  Y is a hydroxyl, alkoxyl, alkyl or nitro group
  "m" is the number of Y substituents 0 or 1
  "n" equals 1–20

U and T are methyl radicals or hydrogen atoms acting strongly towards pathogenic fungi, especially of the Alternaria and Botrytis genera.

2 Claims, No Drawings

QUATERNARY BENZYLMORPHOLINE SALTS HAVING FORMYL OR NITRILE SUBSTITUENTS IN A RING AND FUNGICIDAL COMPOSITIONS

RELATED APPLICATION

This is a continuation-in-part of Application Ser. No. 42,406, filed May 25, 1979, which, in turn, was a divisional of application Ser. No. 954,305, filed Oct. 24, 1978, abandoned.

This invention relates to the group of quaternary benzylmorpholine salts having formyl or nitrile substituents in a ring, acting towards fungi, and to the method of their preparation.

Our invention has as an object a synthesis of compounds having fungicidal action, especially for controlling pathogens causing plant diseases, including the pathogens immune against the action of plant protecting agents used hitherto, such as carbendazime (2-benzimidazolecarbamic acid methyl ester); methylthiophanate (1,2-bis-(3-methoxy-carbonyl-2-thio-ureido)-benzene; tridemorph (N-tridecyl-2,6-dimethyl morpholine).

However, it has been stated that repeated use of these effective, though very selective, fungicides causes changes in plant parasite microflora. Destroyed pathogens are replaced by others, as from Alternaria genus, giving rise to difficult plant diseases. Furthermore, some pathogens, as Botrytis s.p., easily developed resistance against the above fungicides. The Botrytis genus is responsible for very serious strawberry, raspberry and grape-vine diseases, substantially reducing (even to zero) crop yields.

Unexpectedly, it has been found that this object was achieved by the compounds with the general formula (1)

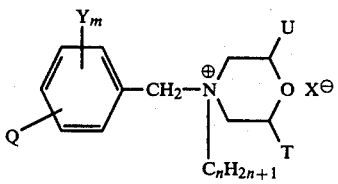

where:
X is a halogen atom
Q is a formyl or nitrile group
Y is a hydroxyl, alkoxyl, alkyl or nitro group
"m" is the number of Y substituents 0 or 1
"n" equals 1-20
U and T are methyl radicals or hydrogen atoms The compounds of general formula (1) may be prepared by quaternization of tertiary amines with formula

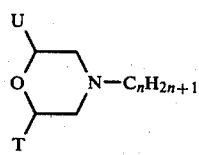

where:
U, T and "n" have the above meanings, with benzyl halides having $Y_m$ and Q substituents in a ring. The reaction is carried out in organic solvents or solvent mixtures.

Said compounds may be also prepared by quaternization of benzylmorpholine having formula

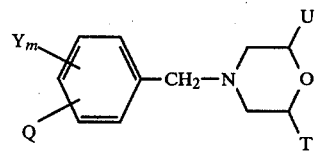

where Y, Q, U, T and "m" have the above meanings, with alkyl halides having formula $C_nH_{2n+1}X$, where X and "n" have the above meanings. The reaction is carried out in organic solvents or solvent mixtures.

Compounds with the general formula (1) have, in general typical, chemical properties of quaternary benzylmorpholine salts and are soluble in water. An advantage of these compounds is the simplicity of their application arising from solubility in water. Thus, they can be easily used in the field of plant protection.

Specific examples of the preparation of the compounds of this invention follow:

EXAMPLE I 18,4 g (0,1 mole) of 5-chloromethyl-2-methoxybenzaldehyde are placed in a flask of 150 cm³ capacity. 28,6 g of N-tetradecylmorpholine and 40 cm³ of benzene are added, and the whole is heated under a reflux condenser during 10 hours. The resulting N-(3-formyl-4-methoxybenzyl)-N-tetradecylmorpholino chloride is filtered off, obtaining 26,5 g (56,5% of a theoretical yield) with a melting point 140°–143° C. - after crystallization from acetone.

EXAMPLE II 18,4 g (0,1 mole) of 5-chloromethyl-2-methoxybenzaldehyde and 31,1 g (0,1 mole) of N-hexdecylmorpholine are placed in a flask of 150 cm³ capacity. 50 cm³ of benzene are added. The mixture is kept at the boiling point during 10 hours. The resulting N-hexadecyl-N-(3-formyl-4-methoxybenzyl)-morpholino chloride is filtered off, obtaining 32,2 g (69% of a theoretical yield), with a melting point 169°–172° C.

EXAMPLE III 15,1 g (0,1 mole) of 4-chloromethylbenzonitrile, 18,5 g (0,1 mole) of N-heptylmorpholine and 50 cm³ of acetonitrille are heated at the boiling point during 5 hours. The resulting N-(4-cyanobenzyl)-N-heptylmorpholine chloride is filtered off, obtaining 29 g (86,3% of a theoretical yield) with a melting point 163°–165° C.

EXAMPLE IV 15,1 g (0,1 mole) of 4-chloromethyl-benzonitrile, 19,9 g (0,1 mole) of N-octylmorpholine and 50 cm³ of benzene are heated at the boiling point during 10 hours. The resulting N-(4-cyanobenzyl)-N-octylmorpholine chloride is filtered off, obtaining 32 g (91% of a theoretical yield) with a melting point 165,5°–166,5° C.—after crystallization from acetone. Effectiveness of the fungicidal action of the compounds with general formula (1) was tested on fungi from the Alternaria and Botrytis genera and compared against effectiveness of carbendazime, methylthiophanate, tridemorph.

The tests were carried out in vitro on Alternaria tenuis spores from a 4 day culture and Botrytis cinerea from a 14 day culture. Results are given in table 1. As a measure of effectiveness was taken the lowest concentration completely inhibiting spore germination.

TABLE 1
Effectiveness of the compounds with the general formula(1)

| No. | Q | Y | X | n | Spore germination inhibiting concentration in ppm | |
|---|---|---|---|---|---|---|
| | | | | | Alternaria tenuis | Botrytis cinerea |
| 1 | 2 | 3 | 6 | 7 | 8 | 9 |
| 1. | 3-CHO | 4-OCH$_3$ | Cl | 1 | >1000 | >1000 |
| 2. | 3-CHO | 4-OCH$_3$ | Cl | 7 | >1000 | >1000 |
| 3. | 3-CHO | 4-OCH$_3$ | Cl | 8 | 1000 | 1000 |
| 4. | 3-CHO | 4-OCH$_3$ | Br | 8 | 1000 | 1000 |
| 5. | 3-CHO | 4-OCH$_3$ | Cl | 10 | 100 | 100 |
| 6. | 3-CHO | 4-OCH$_3$ | Cl | 12 | 100 | 100 |
| 7. | 3-CHO | 4-OCH$_3$ | Cl | 14 | 100 | 100 |
| 8. | 3-CHO | 4-OCH$_3$ | Cl | 16 | 100 | ±10 |
| 9. | 3-CHO | 6-OCH$_3$ | Cl | 7 | 1000 | 1000 |
| 10. | 3-CHO | 6-OCH$_3$ | Cl | 8 | 1000 | 1000 |
| 11. | 3-CHO | 6-OCH$_3$ | Cl | 10 | ±100 | ±100 |
| 12. | 3-CHO | 6-OCH$_3$ | Cl | 12 | 100 | 100 |
| 13. | 4-CHO | H | Cl | 1 | >1000 | >1000 |
| Carbendazime | | | | | >1000 | ±10 |
| Methylthiophanate | | | | | >1000 | ±10 |
| Tridemorph | | | | | >1000 | >1000 |

The agents, according to the present invention, may be applied as an aqueous solution, wettable powder, concentrated powder for dusting, emulsion solution, paste or tablets.

This may be achieved by mixing the biologically active substance with appropriate mineral or organic carriers as kaolin, synthetic or natural kieselguhr, bentonite, talc, grain flourwood bark or walnut shell flours, powdered chitin and others; thinners or solvents as water, methanol, ethanol, ethylene glycol and surface-active agents, emulsifiers, dispersers and wetting agents as ammonium, alkali or alkaline earth metal salts, lignin sulphonic acids, alkyl or aryl sulphonic derivatives, N-methyl-taurine derivatives or products of ethylene oxide addition to fatty alcohols, fatty acids or higher aromatic or aliphatic amines.

The final product may also contain buffers, densifiers, adhesive agents, antifoaming agents and colors.

The agents according to the present invention may be introduced into molded materials for encapsulation of seeds prepared fow sowing. They may be also applied as additives for paints, lacquers, other polymers and also for impregnating wood against destructive microorganism action.

An advantage of the agents is the simplicity of their application arising from solubility of the active compounds in water. Thus, the fungicides may be easily prepared for use, for instance as a solution for plant spraying.

EXAMPLE V 10 parts by weight of N-dodecyl-N-(2-methoxy-5-formylbenzyl)-dimethylamine chloride are mixed with 0,3 part by weight of alkylarylpolyglycol ether and 89,7 parts by weight of distilled water. Such a formulation, tested in the liquid form in concentrations of 1-100 ppm of the active compound, very efficiently inhibited germination of Alternaria tenuis and Botrytis cincerea spores.

EXAMPLE VI 50 parts by weight of N-hexadecyl-N-(3-formyl-4-methoxybenzyl)-morpholine chloride are mixed with 40% kieselguhr, 2% wetting agent+8% disperser (waste calcium sulphite liquor). The resulting wettable powder is diluted with water to concentrations of 10-100 ppm of the active compound. Such suspensions completely inhibited germination of Alternaria tenuis and Botrytis cinerea spores.

What is claimed:
1. Compounds having the formula:

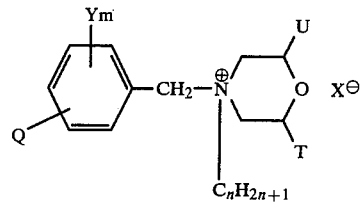

where:
X is a halogen atom
Q is a formyl or nitrile (cyano) group
Y is a hydroxyl, alkoxyl, alkyl or nitro group
"m" is 0 or 1
"n" equals 1–20
U and T are methyl radicals or hydrogen atoms.

2. A fungicidal composition wherein the active ingredient has the general formula:

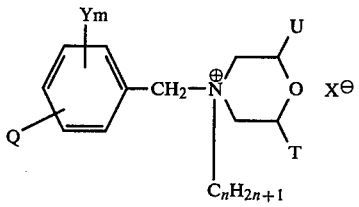

wherein
X is a halogen atom,
Q is a formyl or nitrile (cyano) group,
Y is a hydroxyl, alkoxyl, alkyl or nitro group,
m is 0 or 1,
n is 1–20, and
U and T are methyl radicals or hydrogen atoms, together with a carrier selected from the group consisting of kaolin, kieselguhr, bentonite, talc, grain flour, wood bark flour, walnut shell flour and powdered chitin, the concentration of said active ingredient in use being from 1 to 100 ppm.

* * * * *